United States Patent [19]

Hashizume et al.

[11] Patent Number: 4,571,434

[45] Date of Patent: Feb. 18, 1986

[54] OLIGO-IMINO-AMINES POSSESSING PLANT-PHYSIOLOGICAL ACTIVITIES AND PROCESS FOR PREPARING THE SAME

[75] Inventors: Takeshi Hashizume; Hiroshi Onoda, both of Tokyo, Japan

[73] Assignee: Nihon Tokusan Kabushiki Kaisha, Tokyo, Japan

[21] Appl. No.: 503,504

[22] Filed: Jun. 13, 1983

[30] Foreign Application Priority Data

Jun. 24, 1982 [JP] Japan .................................. 57-107620

[51] Int. Cl.$^4$ .................. C07C 119/00; C07C 125/08; C07C 125/00
[52] U.S. Cl. .................................................... 564/103
[58] Field of Search .......................................... 564/103

[56] References Cited

U.S. PATENT DOCUMENTS

| | | | |
|---|---|---|---|
| 2,418,696 | 4/1947 | Cameron et al. ............... | 564/103 X |
| 3,257,169 | 6/1966 | Sprague .......................... | 564/103 X |
| 3,733,360 | 5/1973 | Firth et al. ...................... | 564/103 X |

FOREIGN PATENT DOCUMENTS 0088047  2/1983  European Pat. Off. ............ 564/103

*Primary Examiner*—Paul F. Shaver

[57] ABSTRACT

Oligo-imino-amines possessing plant-physiological activities and process for preparing the same are provided. Said substance is represented by the general formula.

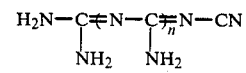

or

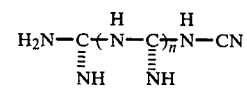

Wherein n=4−6.

2 Claims, 1 Drawing Figure

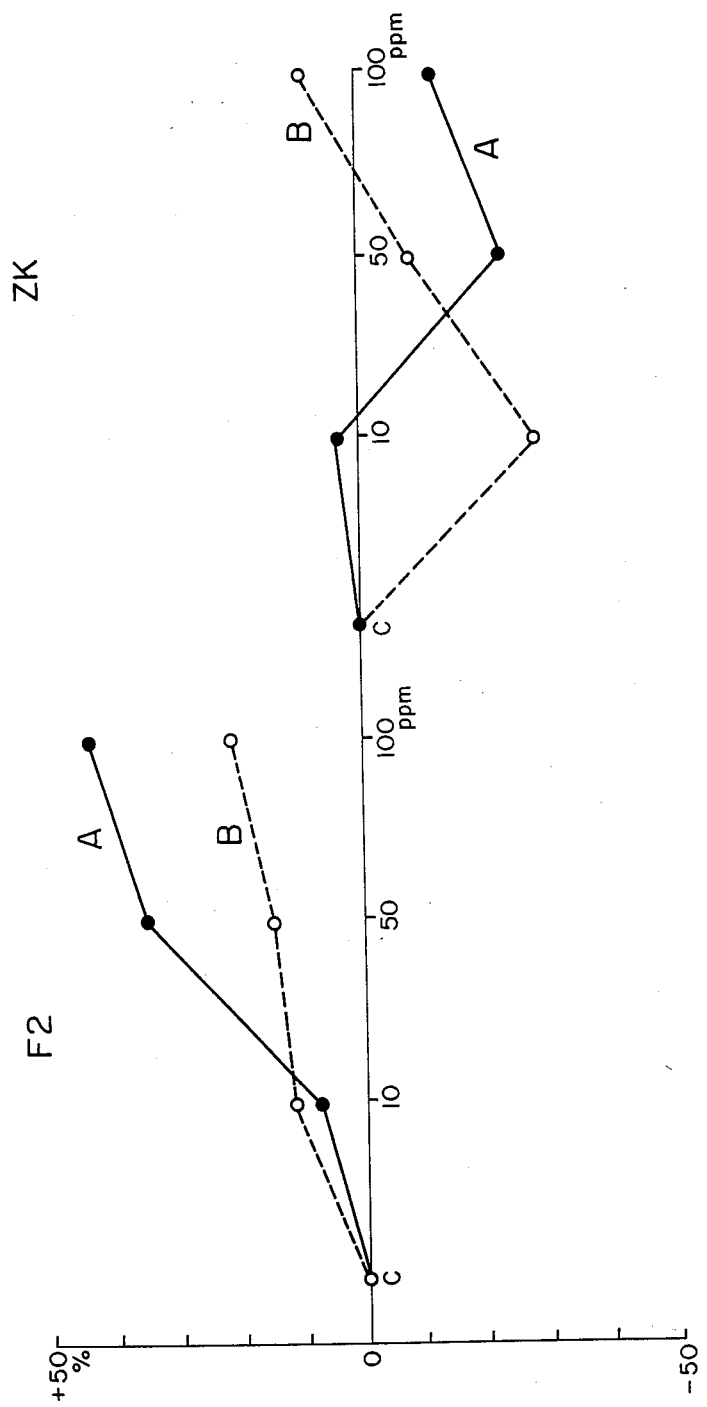

OLIGO-IMINO-AMINES POSSESSING PLANT-PHYSIOLOGICAL ACTIVITIES AND PROCESS FOR PREPARING THE SAME

BACKGROUND OF THE INVENTION

The present invention relates to oligo-imino-amines which are new plant-physiologically active substances formed by heating dicyanodiamide, cyanamide, guanylurea or salt thereof and a process for preparing the same.

In order for human being to exist on the earth over the remote future, food and energy resources should be secured. Biomass has become the focus of public attention as a regenerative energy source which forms a part of the resources. In other words, it represents fixing solar energy into plant bodies as much as possible for which it is necessary to achieve increase in productivity of plants.

A variety of physiologically active substances participate in the normal growth of plants. In addition to known plant hormons such as auxins, gibberellins, cytokinins, abscisic acid, and the like. Various vitamins, stevioside which is a component of stevia, for example, has recently been found to exhibit growth promoting activities toward plant. In addition to the above, a wide variety of physiologically active substances presumably exist, and it is conceivable that potential productive capacity of the plant can be actualised by adequately controlling the levels of these substances to increase the productivity.

SUMMARY OF THE INVENTION

We have carried out search from the above-mentioned point of view for novel substances exerting physiological activities in the plant, particularly cell division-promoting activites and antiviral activities. In the course of the search we have found that substances possessing both cytokinin activities and antiviral activities are obtained by the heat treatment of diamide lime (containing 97% or less CaCO3), a byproduct in the preparation of dicyanodiamide from calcium cyanamide under normal or elevated pressure.

In order to elucidate nature of the activities, the active component was subjected to separation and purification by the extraction with organic solvents and a variety of chromatographic procedures. Analysis of the chemical structure was carried out by means of infrared spectroscopy, mass spectrometry and $^1H$ and $^{13}C$ nuclear magnetic resonance spectroscopy to determine that it was dicyandiamide oligomers. They are novel substances heretofore undisclosed. Furthermore, investigations were made for the process to prepare the active substances efficiently. As a result of the inverstigations, it was found that they are produced in relatively high yields from dicyandiamide, cyanamide, guanylurea or a salt thereof. The present invention was completed on the basis of the abovementioned finding.

As a matter of fact, the novel substances of the invention which possess plant-physiological activities are represented by the general formula

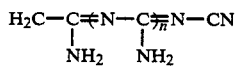

or

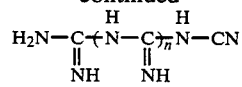

wherein n=4–6.

The oligo-imino-amines are obtained by heating dicyandiamide, cyanamide, guanylurea or a salt thereof under ordinary or elevated pressure.

BRIEF DESCRIPTION OF THE DRAWING

The FIGURE is graphs indicating the effects of the oligoimeno-amines of the invention on TMV—infected tomato cultivar. The percent viral level is shown in the drawing in which curve A is for OIA monomer prior to heat condensation whereas curve B is for OIA after heat condensation.

DETAILED DESCRIPTION OF THE EMBODIMENT

Next, the present invention will be described in embodiment. We have found that when the above-mentioned diamide lime is heated at 80°–220° C. under pressure for several to 10 min., a certain minor component present in the diamide lime in a minimum quantity are subjected to chemical change to be converted to a physiologically active substance favorable for the growth of plants as described in detail later. In fact, the diamide lime heat-treated under the conditions as set forth above is extracted with boiling water and boiling alcohol. The crude extract and a substance obtained by further purification by means of a high performance-liquid chromatography were tested for cytokinin activity in terms of variation in betacyanin biosynthesizing activity using Amaranthus Caudatus. As a result of the test, it was found that these substances exhibited cytokinin activities in concentrations in the range between 0.1 and 0.0017%.

Also, when dicyandiamide, cyanamide, guanylurea or a salt thereof was heated at 100°–250° C. and a pressure from ordinary one to 6 atms and the heat and pressur reaction product was extracted and purified, the substances thus obtained had cytokinin activities.

Moreover, when the above-mentioned substances were tested for effect on the viral level in tomato of the cultivars Fukuju No. 2 and Zuiko infected with tobacco mosaic virus (called TMV for short hereinbelow). It was found that the substances possessed activities to reduce the viral level in concentrations in the range from 10 to 100 ppm.

The invention will be described below by giving examples.

EXAMPLE 1

Diamide lime which was a byproduct in the production of dicyandiamide from calcium cyanamide was heat-treated at 100°–300° C. Two Kg. of the product was heated in 2 l. of boiling water under reflux for 7–10 hours. The reaction mixture was filtered hot, and the filtrate was allowed to cool to give 2.5 g. of colorless precipitates. The product showed a week cytokinin activity in the Amaranthus betacyanin bioassay. However, as it was found to contain a large quantity of inorganic materials, purification was carried out as described below.

To 2.5 g. of the crude product were added 150 ml. of freshly distilled methanol, and the mixture was heated on a water bath at 75° C. The solution was filtered hot to remove insoluble materials. The pale yellow clear filtrate thus obtained was rotoevaporated under reduced pressure until crystals began to form. The crystals formed, which weighed 600 mg., melted at 209°-210° C. was identified as dicyandiamide by means of infrared spectroscopy and mixed melting point test. The crystals were removed by filtration and the filtrate was further evaporated under reduced pressure. When allowed to cool, the second crop of crystals were formed and removed. The filtrate was further evaporated under reduced pressure, and the orange colored-residual solution was allowed to cool to obtain final crystals (280 mg., m.p. 207°-210° C.). An Amaranthus betacyanine bioassay was conducted for an aliquot (0.04 ml.) of the filtrate (ca. 4 ml.) to observe a high cytokinin activity. The filtrate was also subjected to silicagel (Merck & Co., GF$_{254}$, 0.25 mm.) chromatography (Solvent, the upper layer of ethyl acetate: 1—propanol:-water=4:1:2, v/v; detection ultraviolet lamp) to observe ultraviolet-absorbing spots respectively at an Rf-value of 0, 0.35, 0.75 and 0.95. Then, the above-mentioned filtrate was subjected to preparative thick-layer chromatography (Silica gel GF$_{254}$, 0.5 mm., the same solvent as above). The four ultraviolet-absorbing bands were scraped out, and elution was made with ethanol until no ultraviolet absorption was observed. Each of the eluates was evaporated to dryness under reduced pressure. There were obtained (1) 2.0 mg., (2) 23.4 mg., (3) 146 mg. and (4) 3 mg. of crystals, respectively. Aqueous solutions in concentration from 0.1% to 0.01% were prepared with each of the crystals (1) to (4), for which the Amaranthus betacyanin assay was conducted. The crystals (2) and (3) showed cytokinin activities, especially the activity of the crystals (3) being comparable to that of benzyladenine and that of the crystals being weaker. Then, physicochemical properties were determined to give the following spectral data:

M.P.: 195°-197° C.

Ultraviolet absorption maxima:

$\lambda_{max}.^{CH3OH}$ 265 nm; $\lambda_{max}.^{0.05N-NaOH-MeOH}$ 265 nm.

Infrared absorption spectrum: $\nu_{max}.^{nujol}$(cm.$^{-1}$) 3350(—NH$_2$str.); 3100(—N+Hstr.); 2250 (C≡Nstr.); 2200(conjugated C≡Nstr.); 1656(N—Hdef.)1636-(N—Hdef.); 1624(N—Hdef.); 1580: 1550(N—Hdef scissorin) 1250(C—Nstr.); 924(N—Hdef wagging).

Mass spectrum(direct introduction method): m/z 336(M); 294; 208; 149; 126(trimer);

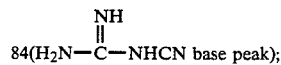
84(H$_2$N—C—NHCN base peak);

68; 43(H$_2$N—C≡N+H); 42(H$_2$N—C≡N).

$^1$H—NMR: Solvent DMSO-d$_6$, 200 MHz, δ 6.65 ppm (S, —NH$_2$, deutrium exchangeable).

$^{13}$C—NMR: Solvent DMSO-d$_6$, JEOL-FX200 (instrument used) δ

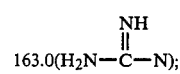
163.0(H$_2$N—C—N);

152.7; 140.2; 139.4; 128.5; 127.4; 127.0 (the 6 carbon atoms cited represent intermediate guanidyl carbon atoms, respectively); 118.7(C≡N) ppm.

The Mass spectrum cited above indicated that molecular weight of the component (3), one of the important components of the active substances in question is 336.

The $^{13}$C—NMR spectrum indicates presence of eight varieties of C atoms, among which one carbon atom (δ 163.0 ppm) is assigned to the terminal

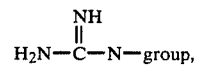
H$_2$N—C—N—group, the carbon atom with δ 118.7 ppm is assigned to that of —C≡N group and six carbon atoms with δ 152.7-127.0 ppm are assigned to guanidyl carbons atoms between the terminal guanidyl group and the cyano group. The presumptions are supported by the infrared spectrum.

Cytokinin Activity

This substance was tested for cytokinin activity by the Amaranthus betacyanin assay. The 0.01% aqueous solution was equivalent to 0.83×10$^{-6}$ mol. in terms of benzyladenine which is a typical synthetic cytokinin.

Effect on the Viral Level in Tomato Infected with TMV

As the test cultivars of tomato were used Fukuju No. 2(F$_2$), a TMV—sensitive cultivar and Zuiko(ZK), a resistant cultivar. Test solutions of the substance of the invention (concentration 10-100 ppm) were absorbed from the root of tomato. After incubation at 25° C. for 7 days in an incubater under 3000 lux the TMV level was chemically determined. It was found that the viral level was reduced by ca. 30% in the resistant cultivar as shown in the attached figure. In addition, Kidnoy-bean half leaves were applied with the substance of the invention in the same concentrations as above and innoculated with the virus with the result that high inhibition of the infection as high as ca. 90% was observed.

EXAMPLE 2

A mixture of 10 g of guanylurea, 2 g of active carbon (manufactured by Takeda Chemical Industries, Carboraffin) and 100 ml. of water was stirred throughly and the mixture was heated in an autoclave at 120° C. and 1.4 atoms. for approximately 15 min. After allowed to cool to ambient temperature, the reaction mixture was taken out and air dried. After air dried, 50 ml. of 97% ethanol was added to the resulting mass, and the mixture was heated under reflux for 2 hours. Insoluble materials (containg the active carbon) was removed by filtration and the alcohol solution was rotoevaporated to dryness under reduced pressure in a rotary evaborator below 50° C. to dryness. The product thus obtained was factionated and purified in the same way as in Example 1 to yield 1.5 mg. of crystals melting at 195°-197° C.

Cytokinin activity of the crystals was assayed by the betacyanin biosynthesis test using *Amaranthus caudatus* cv early splender. As shown in Table-1, high cytokinin activities were observed.

TABLE 1

Results of the cytokinin activity assay.
(The assay method employed is that reported by Biddington, and Thomas in Planta)

| Absorbance | A$_{542}$ | A$_{620}$ | A$_{542}$-A$_{620}$ |
|---|---|---|---|
| Control 1 | 0.111 | 0.052 | 0.059 |
| Control 2 | 0.099 | 0.046 | 0.053 |
| Control 3 | 0.102 | 0.051 | 0.051 |

TABLE 1-continued

Results of the cytokinin activity assay.
(The assay method employed is that reported
by Biddington, and Thomas in Planta)

| Absorbance | $A_{542}$ | $A_{620}$ | $A_{542}-A_{620}$ |
|---|---|---|---|
| Benzyladenine ($0.25 \times 10^{-5}$ mol.)1 | 0.440 | 0.146 | 0.294 |
| Benzyladenine ($0.25 \times 10^{-5}$ mol.)2 | 0.383 | 0.102 | 0.281 |
| Product of the invention (0.067% aqueous solution) | 0.428 | 0.122 | 0.306 |

A represents the absorbance.
$A_{542}$ represents the absorbance at a wave length of 542 nm.

EXAMPLE 3

Fifteen grams of guanylurea, 2 g. of active carbon, anhydrous silicic acid (manufactured by Koizumi Kagaku Yakuhin & Co.) and 100 ml. of water were mixed throughly. The mixture was placed in an autoclave and heated under pressure at 120° C. for 15 min. After allowed to cool to ambient temperature, the resulting mixture was subjected to extraction with ethanol and separation by preparative thick layer chromatography in the same way as in Example 2. Yield of the cytokinin active substance was 60 mg.

As a result of investigations on the reaction temperature and pressure in the autoclave mentioned above, it was found that the range between 120° C. (1.4 atms.) and 210° C. (6 atms.) was optimal.

EXAMPLE 4

To 5 g of guanylurea phosphate and 50 g of diamide lime was added a small quantity of metallic copper. The mixture was heated at 120° C. for 15 min., followed by allowing to cool. The resulting mixture was heated with 99% ethanol for several hours and then filtered hot. The filtrate was cooled, and the crystals thus formed were separated by filtration. The yield was 300 mg.

The product showed a cytokinin activity as assayed with Amaranthus. Besides, in order to examine the effect of the reaction temperature on the yield, the heating reactions were carried out for 15 min. respectively at 110° C., 120° C., 150° C. 210° C., 220° C. and 260° C. to determine the yield of the active substance. It was found that there was produced no active substances at 110° C. or below and at 220° C. or above, and the temperature of 120° C. was optimal.

Ratio of the quantities of diamide lime and guanylurea phosphate was also investigated. It was observed that, under the above-cited reaction conditions, a ratio by weight of diamide lime:guanylurea phosphate of 3:1 was optimal.

When guanylurea sulfate was used as the starting material and reacted under the conditions cited above, there was obtained no active substance.

EXAMPLE 5

To 50 g of dicyandiamide were added 100 ml. of water and 100 ml. of 10% aqueous solution of ammonia. The mixture was stirred at ca. 80° C. for 30 min. After allowed to cooled, prism crystals formed were washed with water several times and air dried. To 10 g of the crystals were added 2 g of active carbon and 100 ml of water to a blend. The blend was heated in an autoclave under pressure at 120° C. (1.4 atms.) for 15 mon. The resulting mixture was treated in the same way as above to obtain 2.3 g of crystals which were active.

Physiological activities for plants, in addition to the cytokinin activity and the antiviral activity, have been found to include a wide variety of favorable effects on the growth of plants such as differentiation adhesion and thickening of the flower bud for cereals vegetables, flowering plants, flowering trees, orchards, forest trees (sapling), pasture and the like. The substances promote the multiplication of microorganisms in the root system and rhizosphere. The inbitory effects against plant virus diseases which were intractable heretofore are considered to be remarkable advantages. The actions to increase resistance to viral diseases and to inhibit the infections are useful for much increasing efficiency in the culture of potato, tobacco, tomato and the like, for example, by enabling safe culture of the resistant cultivar of egg plant with increased yield.

Multiplication of *Rhizobium meliloti* and useful microorganisms promotes fertilization of the soil and is further considered to contribute to fermentation industry.

What is claimed is:

1. Oligo-imino-amines possessing plant-physiological activities represented by the general formula

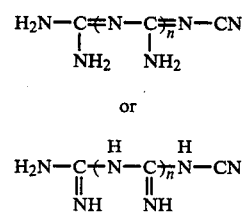

Wherein n=4-6.

2. Process for preparing oligo-imino-amines according to claim 1 which comprises heating a member selected from the group consisting of dicyandiamide, cyanamide, guanylurea or a salt thereof under ordinary or elevated pressure.

* * * * *